United States Patent [19]

Carr et al.

[11] 3,931,197

[45] *Jan. 6, 1976

[54] SUBSTITUTED PIPERIDINE DERIVATIVES

[75] Inventors: Albert A. Carr; C. Richard Kinsolving, both of Cincinnati, Ohio

[73] Assignee: Richardson-Merrell Inc., Wilton, Conn.

[ * ] Notice: The portion of the term of this patent subsequent to Apr. 23, 1991, has been disclaimed.

[22] Filed: Feb. 8, 1974

[21] Appl. No.: 440,856

[52] U.S. Cl. .............. 260/293.62; 260/247.5 G; 260/268 PH; 260/293.64; 260/293.68; 260/293.71; 260/293.79; 260/293.8; 424/248; 424/250; 424/267
[51] Int. Cl.² .................................. C07D 211/22
[58] Field of Search . 260/247.5 G, 268 PH, 293.62, 260/293.64, 293.68, 293.71, 293.79, 293.8

[56] References Cited
UNITED STATES PATENTS

| | | | |
|---|---|---|---|
| 3,438,991 | 4/1969 | Janssen | 260/293.8 |
| 3,806,526 | 4/1974 | Carr et al. | 260/293.8 |
| 3,829,433 | 8/1974 | Carr et al. | 260/293.8 |

*Primary Examiner*—Sherman D. Winters
*Attorney, Agent, or Firm*—L. Ruth Hattan; E. O. Retter; G. W. Rauchfuss, Jr.

[57] ABSTRACT

Novel compounds useful as antihistamine agents, antiallergy agents, and bronchodilators are represented by the following formula

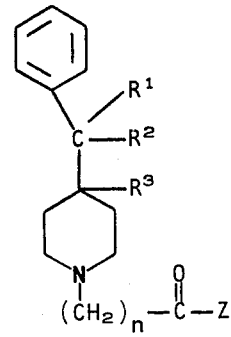

wherein $R^1$ represents cyclohexyl, phenyl, or substituted phenyl wherein the substituent on the substituted phenyl is selected from halogen, a straight or branched lower alkyl group of from 1 to 4 carbon atoms, or a lower alkoxy group of from 1 to 4 carbon atoms; $R^2$ represents hydrogen or hydroxy; $R^3$ represents hydrogen; or $R^2$ and $R^3$ taken together form a second bond between the carbon atoms bearing $R^2$ and $R^3$; $n$ is an integer of from 1 to 3; Z represents thienyl, naphthyl, phenyl, or substituted phenyl wherein the substituent on the substituted phenyl may be attached at the ortho, meta or para position of the phenyl ring and is selected from halogen, a straight or branched alkyl group of from 1 to 6 carbon atoms, an alkoxy group of from 1 to 6 carbon atoms, a cycloalkyl group of from 3 to 6 carbon atoms, di(lower)alkylamino, or a saturated monocyclic heterocyclic group such as pyrrolidino, piperidino, morpholino, or N-(lower)alkylpiperazino with the proviso that when $R^1$ is phenyl, Z is naphthyl or phenyl substituted with a straight or branched alkyl group of 5 or 6 carbon atoms, a lower alkoxy group of 5 or 6 carbon atoms, or a cycloalkyl group of from 3 to 6 carbon atoms. Pharmaceutically acceptable acid addition salts and individual optical isomers of compounds of the above formula are also included as a part of this invention.

14 Claims, No Drawings

SUBSTITUTED PIPERIDINE DERIVATIVES

FIELD OF INVENTION

This invention relates to novel substituted piperidine derivatives which are useful as antihistamine agents, antiallergy agents and bronchodilators and to methods of making and using the same.

BACKGROUND OF INVENTION

Belgian Pat. No. 794,595 which is equivalent to U.S. application Ser. No. 221,823 filed Jan. 28, 1972, now U.S. Pat. No. 3,806,526 describes compounds useful as antihistamine agents, antiallergy agents and bronchodilators having the formula

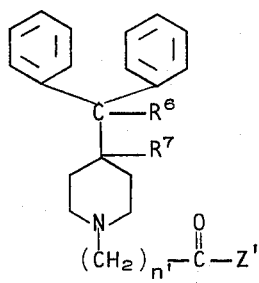

wherein $R^6$ represents hydrogen or hydroxy; $R^7$ represents hydrogen; or $R^6$ and $R^7$ taken together form a second bond between the carbon atoms bearing $R^6$ and $R^7$; $n'$ is a positive whole integer of from 1 to 3; $Z'$ represents thienyl, phenyl, or substituted phenyl wherein the substituents on the substituted phenyl may be attached at the ortho, meta, or para positions of the phenyl ring and are selected from halogen, a straight or branched lower alkyl group of from 1 to 4 carbon atoms, a lower alkoxy group of from 1 to 4 carbon atoms, di(lower)alkylamino, or a saturated monocyclic heterocyclic group such as pyrrolidino, piperidino, morpholino, or N-(lower)alkylpiperazino. Pharmaceutically acceptable acid addition salts and individual optical isomers of compounds of the above formula are also disclosed.

SUMMARY OF INVENTION

The novel substituted piperidine derivatives of this invention are useful as antihistamine agents, antiallergy agents and bronchodilators and are represented by the formula

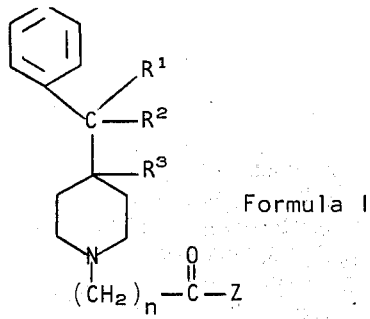

Formula I wherein $R^1$ represents cyclohexyl, phenyl, or a substituted phenyl ring wherein the substituent on the substituted phenyl ring is attached at the ortho, meta or para position of the phenyl ring and is selected from halogen, a straight or branched lower alkyl group of from 1 to 4 carbon atoms, or a lower alkoxy group of from 1 to 4 carbon atoms; $R^2$ represents hydrogen, or hydroxy; $R^3$ represents hydrogen; or $R^2$ and $R^3$ taken together form a second bond between the carbon atoms bearing $R^2$ and $R^3$; $n$ is an integer of from 1 to 3; $Z$ represents thienyl, naphthyl, phenyl, or a substituted phenyl ring wherein the substituent on the substituted phenyl ring is attached at the ortho, meta or para position of the phenyl ring and is selected from halogen, a straight or branched alkyl group of from 1 to 6 carbon atoms, an alkoxy group of from 1 to 6 carbon atoms, a cycloalkyl group of from 3 to 6 carbon atoms, di(lower)alkylamino, or a saturated monocyclic heterocyclic group such as pyrrolidino, piperidino, morpholino or N-(lower)alkylpiperazino with the proviso that when $R^1$ is phenyl, Z is naphthyl or a substituted phenyl ring wherein the substituent on the substituted phenyl ring is attached at the ortho, meta or para position of the phenyl ring and is selected from a straight or branched alkyl group of 5 or 6 carbon atoms, an alkoxy group of 5 or 6 carbon atoms, or a cycloalkyl group of from 3 to 6 carbon atoms. Pharmaceutically acceptable acid addition salts and individual optical isomers of the compounds of Formula I are included in the scope of this invention.

DETAILED DESCRIPTION OF INVENTION

The compounds of this invention are 4-(disubstitutedmethyl)piperidine derivatives, 4-(disubstitutedmethanol)-piperidine derivatives, or 4-(disubstitutedmethylene)-piperidine derivatives as represented by the following respective Formulas II to IV.

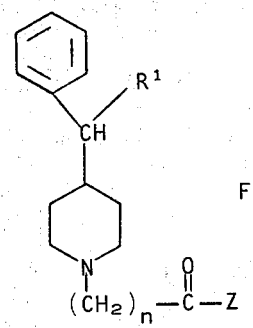

Formula II

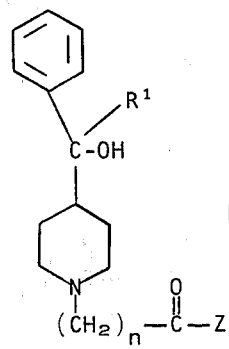

Formula III

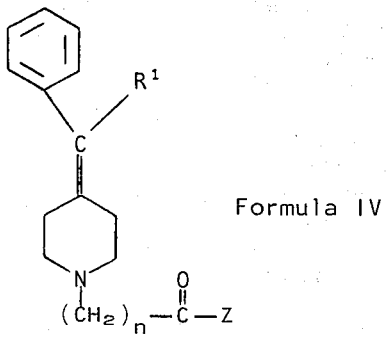

Formula IV

In the above Formulas II, III and IV, $R^1$, $n$, and Z have the meanings described in Formula I.

The term halogen as used herein is taken to mean bromine, chlorine, fluorine or iodine. Preferred halogens are chlorine and fluorine.

Illustrative examples of straight or branched lower alkyl groups of from 1 to 4 carbon atoms that may be present as the substituent on the substituted phenyl as represented by $R^1$ of Formulas I to IV are methyl, ethyl, n-propyl, isopropyl, n-butyl, and tert-butyl.

Illustrative examples of lower alkoxy groups of from 1 to 4 carbon atoms that may be present as the substituent on the substituted phenyl as represented by $R^1$ in Formulas I to IV are methoxy, ethoxy, propoxy and butoxy. Illustrative examples of alkoxy groups of from 1 to 6 carbon atoms that may be present as the substituent on the substituted phenyl as represented by Z in Formulas I to IV are methoxy, ethoxy, propoxy, butoxy, pentyloxy and hexyloxy.

Illustrative examples of straight or branched alkyl groups of from 1 to 6 carbon atoms that may be present as the substituent on the substituted phenyl as represented by Z in Formulas I to IV are methyl, ethyl, n-propyl, isopropyl, isobutyl, tert-butyl, n-butyl, n-pentyl, neopentyl, and n-hexyl. Cycloalkyl as used herein represents cyclopropyl, cyclobutyl, cyclopentyl and cyclohexyl.

The term (lower)alkyl as used in describing the groups di(lower)alkylamino and N-(lower)alkylpiperazino each of which may be the substituent on the substituted phenyl as represented by Z in Formulas I to IV is taken to mean a straight or branched lower alkyl group of from 1 to 4 carbon atoms illustrative examples of which are methyl, ethyl, n-propyl, isopropyl, n-butyl and tert-butyl.

When in Formulas I to IV $R^1$ represents a phenyl group, Z represents naphthyl or a substituted phenyl wherein the substituent on the substituted phenyl may be attached at the ortho, meta or para position of the phenyl ring and is selected from a straight or branched alkyl group of 5 or 6 carbon atoms, an alkoxy group of 5 or 6 carbon atoms, or a cycloalkyl group of 3 to 6 carbon atoms and may be represented by the following Formula V:

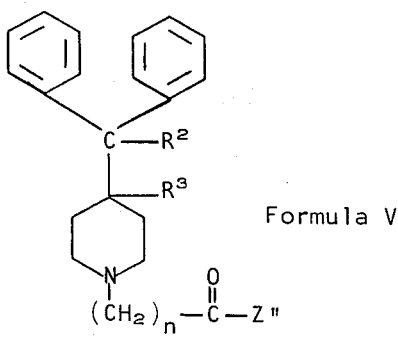

Formula V wherein $R^2$, $R^3$ and $n$ have the meanings defined in Formula I, and Z'' represents naphthyl or a substituted phenyl ring wherein the substituent is selected from a straight or branched alkyl group of 5 to 6 carbon atoms, an alkoxy group of 5 or 6 carbon atoms or a cycloalkyl group of from 3 to 6 carbon atoms and wherein said substituents may be attached at the ortho, meta, or para position of the phenyl ring.

The compounds of this invention as represented by Formulas I to IV wherein $R^1$ represents cyclohexyl or substituted phenyl may be further illustrated by the following respective Formulas VI and VII.

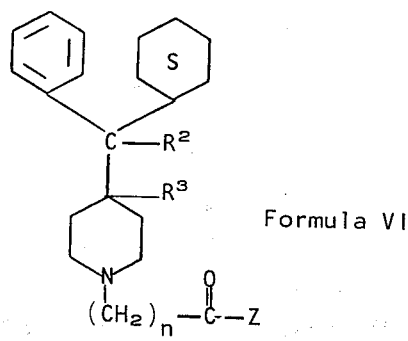

Formula VI

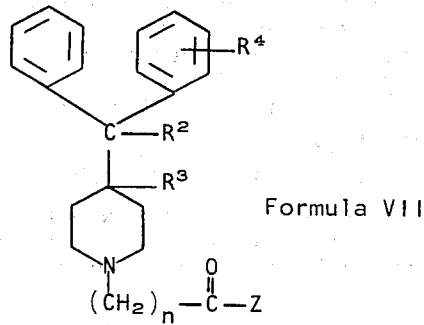

Formula VII

In the above Formulas VI and VII $R^2$, $R^3$, $n$ and Z have the meanings defined in Formula I, and $R^4$ represents halogen, a straight or branched lower alkyl group of from 1 to 4 carbon atoms or a lower alkoxy group of from 1 to 4 carbon atoms.

Preferred compounds of this invention are those wherein $R^1$ represents phenyl or substituted phenyl. More preferred compounds of this invention are those wherein $R^1$ represents phenyl or substituted phenyl and Z is other than naphthyl or thienyl.

This invention also includes the pharmaceutically acceptable acid addition salts of the compounds of the hereinbefore set forth formulas, optical isomers and salts thereof. Pharmaceutically acceptable acid addition salts of the compounds of this invention are those of any suitable inorganic or organic acid. Suitable inorganic acids are, for example, hydrochloric, hydrobromic, sulphuric, phosphoric acids and the like. Suitable organic acids include carboxylic acids such as, for example, acetic, propionic, glycolic, lactic, pyruvic, malonic, succinic, fumaric, malic, tartaric, citric, ascorbic, maleic, hydroxymaleic, and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic acid and the like, sulfonic acids such as, for example, methanesulfonic, ethanesulfonic, β-hydroxyethanesulfonic acid, and the like.

Illustrative examples of compounds of this invention are 4-[4-[α-hydroxy-α-(p-chlorophenyl)benzyl]-piperidino]-butyrophenone, 3-[4-[α-hydroxy-α-(o-ethoxyphenyl)benzyl]-piperidino]propiophenone, 5-[4-[α-(p-tert-butylphenyl)-benzyl]piperidino]-4'-fluorovalerophenone, 2'-dimethylamino-2-[4-[α-(m-methylphenyl)benzylidene]piperidino]-acetophenone, 4-[4-[α-hydroxy-α-(p-fluorophenyl)benzyl]-piperidino]-4'-morpholinobutyrophenone, 4'-cyclopropyl-4-[4-[α-(p-isopropylphenyl)benzyl]-piperidino]butyrophenone, 4-[4-[α-(o-methoxyphenyl)benzylidene]piperidino]-4'-piperidinobutyrophenone, 4-[4-(α-hydroxy-α-phenylbenzyl)-piperidino]-1-(2-naphthyl)butan-1-one, 3-[4-[α-(p-n-butoxyphenyl)benzyl]piperidino]-1-(2-naphthyl)propan-1-one, 3-[4-(α-cyclohexylbenzyl)-piperidino]propiophenone, 4-[4-(α-cyclohexylbenzyl)-piperidino]-4'-fluorobutyrophenone, 3-[4-[α-(p-ethylphenyl)-α-hydroxybenzyl]piperidino]-4'-methylpropiophenone, 2-[4-(α-cyclohexylbenzylidene)-piperidino]-4'-pyrrolidinoacetophenone, 4-[4-(α-cyclohexyl-α-hydroxybenzyl)piperidino]-1-(2-naphthyl)butan-1-one, 4-[4-(α-hydroxy-α-phenylbenzyl)-piperidino]-4'-neopentylbutyrophenone, 4-(4-diphenylmethylenepiperidino)-4'-n-hexylbutyrophenone, 4'-cyclohexyl-3-(4-diphenylmethylpiperidino)-propiophenone, 4-[4-(α-hydroxy-α-phenylbenzyl)-piperidino]-3'-pentoxybutyrophenone, and 4-[4-[α-hydroxyα-(p-bromophenyl)benzyl]piperidino]-1-(2-thienyl)butan-1-one.

The novel compounds of this invention are useful as antihistamines, antiallergy agents and bronchodilators and may be administered alone or with suitable pharmaceutical carriers to warm blooded animals, mammals such as felines, canines, porcine, bovine, equine and humans, and can be in solid or liquid form such as, for example tablets, capsules, powders, solutions, suspensions, or emulsions. The compounds of this invention can be administered orally, parenterally, for example, subcutaneously, intravenously, intramuscularly, intraperitoneally, by intranasal instillation or by application to mucous membranes such as that of the nose, throat, and bronchial tubes, for example, in an aerosol spray containing small particles of a compound of this invention in a spray or dry powder form.

The quantity of novel compounds administered will vary. Depending on the patient and the mode of administration, the quantity of novel compound administered may vary over a wide range to provide in a unit dosage of from about 0.01 to 20 milligrams per kilogram of body weight of the patient per dose to achieve the desired effect. For example the desired antihistamine, antiallergy and bronchodilator effects can be obtained by consumption of a unit dosage form such as, for example, a tablet containing 1 to 100 milligrams of a novel compound of this invention taken 1 to 4 times daily.

The solid unit dosage forms can be of the conventional type. Thus, the solid form can be a capsule which can be of the ordinary gelatin type containing a novel compound of this invention and a carrier, for example, lubricant and inert fillers such as lactose, sucrose, corn starch, and the like. In another embodiment, the novel compounds are tabletted with conventional tablet bases such as lactose, sucrose, corn starch, and the like in combination with binders such as acacia, corn starch or gelatin, disintegrating agents such as corn starch, potato starch, or alginic acid, and a lubricant such as stearic acid, or magnesium sterate.

The novel compounds may also be administered as injectable dosages by solution or suspension of the compounds in a physiologically acceptable diluent with a pharmaceutical carrier which can be a sterile liquid such as water and/or oils, with or without the addition of a surfactant and other pharmaceutically acceptable adjuvants. Illustrative of oils there can be mentioned those of petroleum, animal, vegetable or synthetic origin, for example, peanut oil, soybean oil, mineral oil, and the like. Water, saline, aqueous dextrose, and related sugar solutions, ethanols and glycols such as propylene glycol or polyethylene glycol are illustrative of liquid carriers for injectable solutions.

For use as aerosols the novel compounds in solution or suspension may be packaged in a pressurized aerosol container together with a gaseous or liquified propellant, for example, dichlorodifluoromethane, dichlorodifluoromethane with dichlorodifluoroethane, carbon dioxide, nitrogen, propane, etc. with the usual adjuvants such as co-solvents, and wetting agents, as may be necessary or desirable. The compounds may also be administered in a non-pressurized form such as in a nebulizer or atomizer.

To illustrate the utility of the compounds of this invention the following tabulation indicates the amount of certain representative compounds of this invention required to reduce by 50% wheals induced by intradermal injections of 1γ of histamine into guinea pigs. Each compound was orally administered one hour prior to the histamine injection.

| Compound | | ED$_{50}$, mg/kg |
|---|---|---|
| 4-[4-(α-hydroxy-α-phenylbenzyl)piperidino]-4'-neopentylbutyrophenone hydrochloride | | 0.5 |
| 4'-tert-butyl-4-[4-[α-(p-methylphenyl)benzylidene]-piperidino]butyrophenone hydrochloride | ca. | 10.0 |
| 4'-cyclopentyl-4-[4-(α-hydroxy-α-phenylbenzyl)-piperidino]butyrophenone hydrochloride | | 2.5 |
| 4'-tert-butyl-4-[4-[α-hydroxy-α-(p-methylphenyl)-benzyl]piperidino]butyrophenone hydrochloride | | 6.0 |
| 4-[4-(α-hydroxy-α-phenylbenzyl)piperidino]-1-(2-naphthyl)butan-1-one hydrochloride | | 3.6 |
| 4'-tert-butyl-4-[4-[α-(p-chlorophenyl)-α-hydroxybenzyl]piperidino]butyrophenone hydrochloride | | 27 |

The compounds of this invention may be prepared by several methods. Some of the compounds of this invention are used to prepare other compounds of the invention as will be apparent from the following. The compounds of Formula I may be prepared by reacting a 4-substituted piperidine, compound 1, with an ω-haloalkyl aryl ketone, compound 2, as indicated by the following:

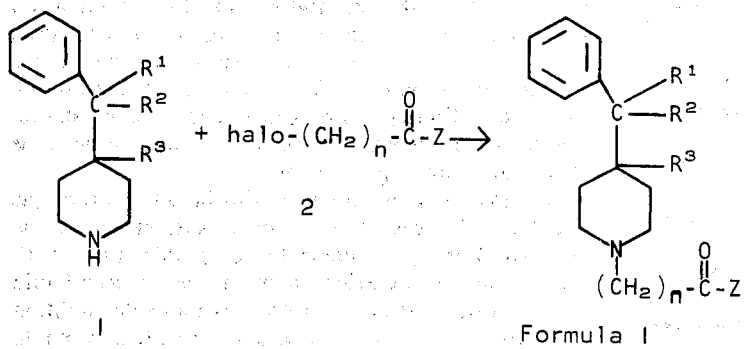

Formula I

In the above reaction halo represents a reactive halogen atom, $R^1$, $R^2$, $R^3$, $n$, and Z have the meanings defined in Formula I.

The above reaction is carried out in alcoholic solvents such as methanol, ethanol, isopropyl alcohol, n-butanol, in ketone solvents such as butanone, methyl isobutyl ketone, and the like, in hydrocarbon solvents such as benzene, toluene, and the like, or in halogenated hydrocarbons, such as chlorobenzene, and the like, in the presence of an inorganic base such as sodium bicarbonate, potassium carbonate and the like, or in the presence of an organic base such as triethylamine, or an excess of compound 1. In some cases it may be desirable to add catalytic amounts of potassium iodide to the reaction mixture. The reaction time is usually about 48 hours, but may vary from about 4 to 120 hours at a temperature of from about 70°C to the reflux temperature of the solvent.

The ω-haloalkyl aryl ketone derivatives, compound 2, are commercially available, or may be prepared by reacting the appropriate ω-haloalkanoyl halide and an aromatic compound in the presence of aluminum chloride. They may also be prepared by reacting a substituted phenyl Grignard reagent with an ω-haloalkanonitrile, followed by the usual work up.

The 4-diphenylmethylpiperidine and α,α-diphenyl-4-piperidinemethanol starting materials as represented by compound 1 wherein $R^1$ is phenyl, $R^2$ is hydrogen or hydroxy, and $R^3$ is hydrogen are commercially available. 4-Diphenylmethylenepiperidine as represented by compound 1 wherein $R^1$ is phenyl and $R^2$ and $R^3$ form a second bond between the carbon atoms bearing $R^2$ and $R^3$ may be prepared by dehydration of α,α-diphenyl-4-piperidinemethanol by generally known procedures.

Starting materials as represented by compound 1 wherein $R^1$ is cyclohexyl or substituted phenyl wherein the substituents are selected from halogen, a straight or branched lower alkyl group of from 1 to 4 carbon atoms, or lower alkoxy of from 1 to 4 carbon atoms, may be prepared by the method described by F. J. McCarty, et al., J. Org. Chem. 26, 4084-8(1961).

The compounds of Formula I wherein n is the integer 2, may also be prepared by a Mannich Reaction of a 4-substituted piperidine derivative with a methyl aryl ketone derivative of the formula

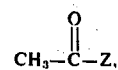

wherein Z has the meaning defined in Formula I, in the presence of formaldehyde. Suitable solvents for this reaction include acetic acid, methanol, ethanol, n-propanol, n-butanol and the like. The reaction is carried out in the presence of a small amount of mineral acid, such as, for example, concentrated hydrochloric acid for about 3 to 24 hours, generally about 8 hours, at a temperature of from about 50°-100°C.

The compounds of Formula I may also be prepared by the reaction of an appropriately 4-substituted 1-piperidinealkanonitrile with an organometallic compound such as an aryl Grignard or an aryllithium compound in a solvent such as diethyl ether or tetrahydrofuran followed by isolation and purification of the aryl 4-substituted piperidinoalkyl ketone derivative by generally known procedures. The nitrile derivative is obtained by the reaction of an appropriately substituted piperidine compound with a haloalkylnitrile.

The compounds of Formula I wherein Z represents a substituted phenyl wherein the substituent on the substituted phenyl is selected from a di(lower)alkylamino group or a saturated monocyclic heterocyclic group and is attached at the ortho- or para- position of the phenyl ring may also be prepared from the corresponding halogen substituted phenyl derivative, preferably a fluoro derivative, using an excess of the dialkylamine or the heterocyclic amine. When volatile amines are employed the amine may be bubbled through a solution of the halogen substituted phenyl derivative in dimethylsulfoxide at about 100°C for about 4 to 8 hours. When higher boiling amines are employed such as, for example, piperidine, excess amounts of the amine are used as base, reactant, and solvent for the reaction which is carried out at the reflux temperature of the amine for about 4 to 24 hours.

The following specific examples are illustrative of the invention.

EXAMPLE 1

4-[4-(α-Hydroxy-α-phenylbenzyl)piperidino]-1-(2-naphthyl)-butan-1-one hydrochloride A mixture of 110 g (0.41 mole) of α,α-diphenyl-4-piperidinemethanol, 110.8 g (0.47 mole) of 4-chloro-1-(2-naphthyl)butan-1-one, 138 g (1.0 mole) of potassium carbonate, 0.2 g of potassium iodide and 500 ml of toluene is stirred and refluxed for 44 hours after which the reaction mixture is diluted with 500 ml toluene, heated to 100°C and filtered. The filtrate is cooled and diluted with an equal volume of dry diethyl ether and treated with ethereal HCl. The resulting precipitate is recrystallized from 1400 ml of ethanol. The first three crops gave α,α-diphenyl-4-piperidinemethanol. The filtrate is diluted with dry diethyl ether to give a precipitate which is crystallized from acetone and further purified by recrystallization from methanol-acetone to give 4-[4-(α-hydroxy-α-phenylbenzyl)-piperidino]-1-(2-naphthyl)butan-1-one hydrochloride, M.P. 206.5°–208.5°C.

EXAMPLE 2

4'-Cyclopentyl-4-[4-(α-hydroxy-α-phenylbenzyl)-piperidino]-butyrophenone hydrochloride A mixture of 27.6 g (0.1 mole) of α,α-diphenyl-4-piperidinemethanol, 30 g (0.12 mole) of 4-chloro-4'-cyclopentylbutyrophenone, 20 g of potassium bicarbonate and 0.1 g of potassium iodide in 250 ml of toluene and 40 ml of water is stirred on a steam bath for 88 hours. Upon cooling to room temperature the toluene layer is separated and the aqueous layer is extracted twice with 50 ml of toluene. The combined organic fractions are washed with water and saturated sodium chloride solution, dried over magnesium sulfate, and filtered. To the filtrate is added two volumes of ether, and the solution is treated with ethereal HCl. The resulting precipitate is collected and recrystallized from methanol-butanone to give 4'-cyclopentyl-4-[4-(α-hydroxy-α-phenylbenzyl)piperidino]butyrophenone hydrochloride, M.P. 232°–234°C.

EXAMPLE 3

4'-tert-Butyl-4-[4-[α-hydroxy-α-(p-tolyl)benzyl]-piperidino]-butyrophenone hydrochloride A mixture of 29.0 g (0.1 mole) of α-phenyl-α-(p-tolyl)-4-piperidinemethanol, 32 g (0.12 mole) of 4'-tert-butyl-4-chlorobutyrophenone, 20 g of potassium bicarbonate, 0.1 g of potassium iodide, 300 ml of toluene and 50 ml of water is stirred on a steam bath for 88 hours. Upon cooling to room temperature the toluene layer is separated, and the aqueous layer is extracted with toluene. The combined toluene fractions are washed with water and saturated sodium chloride solution, dried over magnesium sulfate, filtered and concentrated to an oil. The oily residue is dissolved in dry ether and filtered. The filtrate is treated with ethereal HCl, and the resulting precipitate is collected and recrystallized from methanol-butanone to give 4'-tert-butyl-4-[4-[α-hydroxy-α-(p-tolyl)benzyl]-piperidino]-butyrophenone hydrochloride, M.P. 194°–196.5°C.

EXAMPLE 4

4-[4-(α-Hydroxy-α-phenylbenzyl)piperidino]-4'-neopentyl-butyrophenone hydrochloride When in the procedure of Example 2 an equivalent amount of 4-chloro-4'-neopentylbutyrophenone is substituted for 4-chloro-4'-cyclopentylbutyrophenone, 4-[4-(α-hydroxy-α-phenylbenzyl)piperidino]-4'-neopentylbutyrophenone hydrochloride is obtained, M.P. 227°–229°C.

EXAMPLE 5

4-[4-[α-Hydroxy-α-(p-tert-butylphenyl)benzyl]-piperidino]-butyrophenone hydrochloride A mixture of 12 g (0.0372 mole) of α-phenyl-α-(p-tert-butylphenyl)-4-piperidinemethanol, 7.85 g (0.042 mole) of 4-chlorobutyrophenone, 13.8 g (0.1 mole) of potassium carbonate, and 0.1 g of potassium iodide in 100 ml of toluene is refluxed with stirring for 64 hours. Upon cooling to room temperature the mixture is filtered, and to the filtrate is added an equal volume of ether followed by treatment with ethereal HCl. The resulting precipitate is recrystallized from isopropyl alcohol and from methanolbutanone to give 4-[4-[α-hydroxy-α-(p-tert-butylphenyl)benzyl]piperidino]-butyrophenone hydrochloride, M.P. 228°–230°C.

EXAMPLE 6

4'-tert-Butyl-4-[4-[α-hydroxy-α-(p-chlorophenyl)benzyl]-piperidino]butyrophenone hydrochloride A mixture of 11 g (0.035 mole) of α-phenyl-α-(p-chlorophenyl)-4-piperidinemethanol, 12.5 g (0.05 mole) of 4'-tert-butyl-4-chlorobutyrophenone, 10 g of potassium bicarbonate, 0.1 g of potassium iodide, 100 ml of toluene and 10 ml of water is refluxed with stirring for about 93 hours. Upon cooling to room temperature the mixture is filtered and the toluene layer is separated. The aqueous layer is extracted with toluene. The combined organic fractions are washed with water and saturated sodium chloride solution, dried over magnesium sulfate, and filtered. To the filtrate is added an equal volume of ether followed by treatment with ethereal HCl. The resulting precipitate is collected and recrystallized from methanol-butanone to give 4'-tert-butyl-4-[4-[α-hydroxy-α-(p-chlorophenyl)benzyl]-piperidino]butyrophenone hydrochloride, M.P. 238.5°–240°C.

EXAMPLE 7

4'-tert-Butyl-4-[4-[α-hydroxy-α-(p-tert-butylphenyl)-benzyl]piperidino]butyrophenone hydrochloride A mixture of 25 g (0.0773 mole) of α-phenyl-α-(p-tert-butylphenyl)-4-piperidinemethanol, 22.2 g (0.093 mole) of 4'-tert-butyl-4-chlorobutyrophenone, 25 g of potassium bicarbonate, 0.1 g of potassium iodide, and 250 ml of toluene is refluxed for 64 hours then filtered while still warm. To the filtrate is added an equal volume of ether followed by treatment with ethereal HCl. The resulting precipitate is collected recrystallized from methanol-butanone, and washed with butanone, then ether to give, 4'-tert-butyl-4-[4-[α-hydroxy-α-(p-tert-butylphenyl)benzyl]-piperidino]butyrophenone hydrochloride, M.P. 213.5°–215.5°C.

EXAMPLE 8

4'-tert-Butyl-4-[4-[α-hydroxy-α-(o-anisyl)benzyl]-piperidino]butyrophenone

When in the procedure of Example 7 an appropriate amount of α-phenyl-α-(o-anisyl)-4-piperidinemethanol is substituted for α-phenyl-α-(p-tert-butylphenyl)-4-piperidinemethanol, the precipitate obtained upon treatment with ethereal HCl is converted to the free base and purified by column chromatography on $Al_2O_3$ by eluting with benzeneethyl acetate. The resulting material is recrystallized from acetone-hexane to give 4'-tert-butyl-4-[4-[α-hydroxy-α-(o-anisyl)benzyl]-piperidino]butyrophenone, M.P. 118°–120°C.

EXAMPLE 9

4'-tert-Butyl-4-[4-[α-(p-tolyl)benzylidene]-piperidino]-butyrophenone hydrochloride A mixture of 25.4 g (0.0905 mole) of α-phenyl-α-(p-tolyl)-4-piperidinemethanol, 26.2 g (0.11 mole) of 4'-tert-butyl-4-chlorobutyrophenone, 22 g of potassium bicarbonate, 0.1 g of potassium iodide, 250 ml of toluene, and 40 ml of water is refluxed for 88 hours. Upon cooling to room temperature the toluene layer is separated, and the aqueous layer is extracted with toluene. The combined toluene extracts are dried over magnesium sulfate, filtered and the filtrate is treated with ethereal HCl. The resulting precipitate is filtered, triturated with ether, and recrystallized from butanone-ether to give 4'-tert-butyl-4-[4-[α-(p-tolyl)benzylidene]piperidino]butyrophenone hydrochloride, M.P. 187°–189°C.

EXAMPLE 10

4'-tert-Butyl-4-[4-(α-cyclohexyl-α-hydroxybenzyl)-piperidino]butyrophenone hydrochloride When in the procedure of Example 7, α-cyclohexyl-α-phenyl-4-piperidinemethanol is substituted for α-phenyl-α-(p-tert-butylphenyl)-4-piperidinemethanol, 4'-tertbutyl-4-[4-(α-cyclohexyl-α-hydroxybenzyl)-piperidino]-butyrophenone hydrochloride is obtained, M.P. >260°C.

EXAMPLE 11

4'-Fluoro-4-[4-[α-hydroxy-α-(p-chlorophenyl)benzyl]piperidino]butyrophenone hydrochloride A mixture of 14 g (0.0465 mole) of α-(p-chlorophenyl)-α-phenyl-4-piperidinemethanol, 12 g (0.06 mole) of 4-chloro-4'-fluorobutyrophenone, 16.8 g (0.2 mole) of sodium bicarbonate and a small amount of potassium iodide in 500 ml of toluene is refluxed 60 hours then filtered. The filtrate is concentrated to an oil which is dissoved in ether and treated with ethereal HCl. The resulting precipitate is collected and recrystallized from methanol-ethyl acetate and then methylene chloride to give 4'-fluoro-4-[4-[α-hydroxy-α-(p-chlorophenyl)benzyl]piperidino]butyrophenone hydrochloride, M.P. 154°C (dec.).

EXAMPLE 12

When in the procedure of Example 3 the substituted 4-piperidinemethanol and the substituted ω-haloalkanone listed below are substituted respectively for α-phenyl-α-(p-tolyl)-4-piperidinemethanol and 4'-tert-butyl-4-chlorobutyrophenone, the respective products listed below are obtained.

| Substituted 4-piperidinemethanol | ω-Haloalkanone | Product |
|---|---|---|
| α-phenyl-α-(p-n-propylphenyl)-4-piperidinemethanol | 4-chloro-1-(2-thienyl)-butan-1-one | 4-[4-[α-hydroxy-α-(p-n-propylphenyl)benzyl]piperidino]-1-(2-thienyl)butan-1-one hydrochloride |
| α-(p-n-butoxyphenyl)-α-phenyl-4-piperidinemethanol | 3-chloro-4'-methyl-propiophenone | 3-[4-[α-(p-n-butoxyphenyl)-α-hydroxybenzyl]piperidino]-4'-methyl-propiophenone hydrochloride |
| α,α-diphenyl-4-piperidinemethanol | 2-chloro-4'-n-pentyloxy-acetophenone | 2-[4-(α-hydroxy-α-phenylbenzyl)-piperidino]-4'-n-pentyloxy-acetophenone hydrochloride |
| 4-[α-(p-bromophenyl)benzyl]-piperidine | 4-chloro-4'-methoxy-butyrophenone | 4-[4-[α-(p-bromophenyl)benzyl]-piperidino]-4'-methoxybutyro-phenone hydrochloride |
| 4-[α-(o-tolyl)benzyl]piperidine | 4-chloro-4'-cyclopropyl-butyrophenone | 4'-cyclopropyl-4-[4-[α-(o-tolyl)benzyl]piperidino]-butyrophenone hydrochloride |
| 4-[α-(p-ethylphenyl)benzyl]-piperidine | 4-chloro-4'-fluorobutyro-phenone | 4-[4-[α-(p-ethylphenyl)benzyl]-piperidino]-4'-fluorobutyro-phenone hydrochloride |

EXAMPLE 13

4'-Dimethylamino-4-[4-[α-hydroxy-α-(p-chlorophenyl)-benzyl]piperidino]butyrophenone Through a solution of 19 g (0.04 mole) of 4'-fluoro-4-[4-[α-hydroxy-α-(p-chlorophenyl)benzyl]-piperidino]butyrophenone, obtained by converting the compound of Example 11 to the free base, in 150 ml of dimethylsulfoxide (DMSO) is bubbled dimethylamine for 6 hours at 100°C. Most of the DMSO is removed at reduced pressure at 120°C. The remaining mixture is poured into water and sodium carbonate to which is added a small amount of methanol. The resulting solid is filtered and dissolved in warm methanol and isopropyl alcohol, treated with charcoal, filtered and cooled. Upon cooling a solid forms which is filtered off and recrystallized from acetone-heptane to give the title compound.

EXAMPLE 14

4-[4-[α-(p-Ethylphenyl)benzyl]piperidino]-4'-piperidino butyrophenone

A solution of 14.5 g (0.035 mole) of 4-[4-[α-(p-ethylphenyl)benzyl]piperidino]-4'-fluorobutyrophenone in 100 ml of piperidine is refluxed for 22 hours. The unreacted piperidine is removed under vacuum, and the remaining residue is triturated with water. The water is decanted, the residue is dissolved in methanol and added to a large amount of water. The resulting precipitate is dissolved in ether, dried over magnesium sulfate, treated with charcoal and filtered. The filtrate is concentrated to a solid residue and is recrystallized from ethanol-water to give the title compound.

EXAMPLE 15

4-[4-(Diphenylmethylene)piperidino]-1-(2-naphthyl)-butan-1-one hydrochloride

A mixture of 17.6 g (0.038 mole) of 4-[4-(α-hydroxy-α-phenylbenzyl)piperidino]-1-(2-naphthyl)-butan-1-one hydrochloride, 400 ml of concentrated HCl and 1500 ml of isopropyl alcohol is heated on a steam bath for 16 hours after which the solvent and excess acid are removed at reduced pressure. The remaining residue is recrystallized from isopropyl alcohol and ethyl acetate to give 4-[4-(diphenylmethylene)-piperidino]-1-(2-naphthyl)butan-1-one hydrochloride.

EXAMPLE 16

When in the procedure of Example 15 an appropriate amount of the 4-substituted-piperidino alkanone compounds of Examples 2 through 8 are substituted for 4-[4-(α-hydroxy-α-phenylbenzyl)piperidino]-1-(2-naphthyl)butan-1-one hydrochloride, the following respective products are obtained: 4'-cyclopentyl-4-[4-(diphenylmethylene)piperidino]butyrophenone hydrochloride, 4'-tert-butyl-4-[4-]α-(p-tolyl)benzylidene]-piperidino]-butyrophenone hydrochloride, 4-[4-(diphenylmethylene)piperidino]-4'-neopentyl-butyrophenone hydrochloride, 4-[4-[α-(p-tert-butylphenyl)benzylidene]-piperidino]butyrophenone hydrochloride, 4'-tert-butyl-4-[4-[α-(p-chlorophenyl)benzylidene]-piperidino]butyrophenone hydrochloride, 4'-tert-butyl-4-[4-[α-(p-tert-butylphenyl)benzylidene]-piperidino]butyrophenone hydrochloride, and 4'-tert-butyl-4-[4-[α-(o-anisyl)benzylidene]-piperidino]-butyrophenone hydrochloride.

EXAMPLE 17

An illustrative composition for hard gelatin capsules is as follows:

| | | |
|---|---|---|
| (a) | 4'-cyclopentyl-4-[4-(α-hydroxy-α-phenylbenzyl)piperidino]butyrophenone hydrochloride | 10 mg |
| (b) | talc | 5 mg |
| (c) | lactose | 100 mg |

The formulation is prepared by passing the dry powders of (a) to (c) through a fine mesh screen and mixing them well. The powder is then filled into hard gelatin capsules at a net fill of 115 mg per capsule.

EXAMPLE 18

An illustrative composition for tablet is as follows:

| | | |
|---|---|---|
| (a) | 4-[4-(α-hydroxy-α-phenylbenzyl)-piperidino]-4'-neopentylbutyrophenone hydrochloride | 5 mg |
| (b) | starch | 43 mg |
| (c) | lactose | 60 mg |
| (d) | magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 19

An illustrative composition for an aerosol solution is the following:

| | | Weight per cent |
|---|---|---|
| (a) | 4'-tert-butyl-4-[4-[α-hydroxy-α-(p-chlorophenyl)benzyl]piperidino]butyrophenone hydrochloride | 5.0 |
| (b) | ethanol | 35.0 |
| (c) | dichlorodifluoromethane | 60.0 |

The materials (a), (b) and (c) are packaged in 15 ml stainless steel containers equipped with a metering valve designed to meter 0.2 grams per dose, an equivalent of 10 mg of novel compound (a).

EXAMPLE 20

An illustrative composition for an aerosol suspension is the following:

| | | Weight per cent |
|---|---|---|
| (a) | 4'-tert-butyl-4-[4-[α-hydroxy-α-(o-anisyl)benzyl]piperidino]-butyrophenone (particle size <10μ) | 20.0 |
| (b) | sorbitan trioleate | 0.5 |
| (c) | dichlorodifluoromethane | 39.75 |
| (d) | dichlorodifluoroethane | 39.75 |

The materials (a) to (d) are packaged in 15 ml stainless steel containers equipped with a metering valve designed to meter 50 mg per dose, an equivalent of 10 mg of novel compound (a).

EXAMPLE 21

An illustrative composition for an injectable suspension is the following 1 ml ampul for an intramuscluar injection.

| | | Weight per cent |
|---|---|---|
| (a) | 4'-tert-butyl-4-[4-[α-hydroxy-α-(p-tert-butylphenyl)benzyl]piperidino]-butyrophenone hydrochloride (particle size <10μ) | 1.0 |
| (b) | polyvinylpyrrolidone (M.W. 25000) | 0.5 |
| (c) | lecithin | 0.25 |
| (d) | water for injection to make | 100.0 |

The materials (a) to (d) are mixed, homogenized, and filled into 1 ml ampuls which are sealed and autoclaved 20 minutes at 121°C. Each ampul contains 10 mg per ml of novel compound (a).

The optical isomers of the compounds of this invention may be separated by using a (+) or (−) binaphthylphosphoric acid derivative or a salt of said derivative and an assymetric base by the method described by R.

Viterbo et al., in Tetrahedron Letters No. 48, pp. 4617–4620 (1971).

We claim:

1. A compound selected from a base of the formula

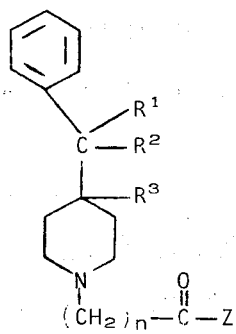

wherein $R^1$ is selected from the group consisting of cyclohexyl, phenyl, and a substituted phenyl ring wherein the substituent on the substituted phenyl ring is attached at the ortho, meta, or para position of the phenyl ring and is selected from the group consisting of halogen, a straight or branched lower alkyl group of from 1 to 4 carbon atoms, and a lower alkoxy group of from 1 to 4 carbon atoms; $R^2$ is selected from the group consisting of hydrogen or hydroxy; $R^3$ represents hydrogen; or $R^2$ and $R^3$ taken together form a second bond between the carbon atoms bearing $R^2$ and $R^3$; n is an integer of from 1 to 3; Z is selected from the group consisting of thienyl, naphthyl, phenyl or a substituted phenyl ring wherein the substituent on the substituted phenyl ring is attached at the ortho, meta or para position of the phenyl ring and is selected from the group consisting of halogen, a straight or branched alkyl group of from 1 to 6 carbon atoms, an alkoxy group of from 1 to 6 carbon atoms, a cycloalkyl group of from 3 to 6 carbon atoms, di(lower)alkylamino, or a saturated monocyclic heterocyclic group selected from the group consisting of pyrrolidino, piperidino, morpholino, and N-(lower)alkylpiperazino with the proviso that when $R^1$ is phenyl, Z is naphthyl or a substituted phenyl ring wherein the substituent on the substituted phenyl ring is attached at the ortho, meta or para position of the phenyl ring and is selected from the group consisting of a straight or branched alkyl group of 5 or 6 carbon atoms, an alkoxy group of 5 or 6 carbon atoms and a cycloalkyl group of from 3 to 6 carbon atoms; and pharmaceutically acceptable acid addition salts thereof.

2. A compound of claim 1 wherein $R^1$ is phenyl.

3. A compound of claim 2 wherein $R^2$ is hydroxy.

4. A compound of claim 3 which is 4-[4-(α-hydroxy-α-phenylbenzyl)piperidino]-1-(2-naphthyl)butan-1-one or a pharmaceutically acceptable acid addition salt thereof.

5. A compound of claim 3 which is 4'-cyclopentyl-4-[4-(α-hydroxy-α-phenylbenzyl)piperidino]butyrophenone or a pharmaceutically acceptable acid addition salt thereof.

6. A compound of claim 3 which is 4-[4-(α-hydroxy-α-phenylbenzyl)piperidino]-4'-neopentylbutyrophenone or a pharmaceutically acceptable acid addition salt thereof.

7. A compound of claim 1 wherein $R^1$ is a substituted phenyl ring.

8. A compound of claim 7 wherein $R^2$ is hydroxy.

9. A compound of claim 8 which is 4'-tert-butyl-4-[4-[α-hydroxy-α-(p-tolyl)benzyl]piperidino]butyrophenone or a pharmaceutically acceptable acid addition salt thereof.

10. A compound of claim 8 which is 4'-tert-butyl-4-[4-[α-hydroxy-α-(p-chlorophenyl)benzyl]piperidino]-butyrophenone or a pharmaceutically acceptable acid addition salt thereof.

11. A compound of claim 8 which is 4'-tert-butyl-4-[4-[α-hydroxy-α-(o-anisyl)benzyl]piperidino]-butyrophenone or a pharmaceutically acceptable acid addition salt thereof.

12. A compound of claim 8 which is 4'-fluoro-4-[4-[α-hydroxy-α-(p-chlorophenyl)benzyl]piperidino]-butyrophenone or a pharmaceutically acceptable acid addition salt thereof.

13. A compound of claim 7 wherein $R^2$ and $R^3$ taken together form a second bond between the carbon atoms bearing $R^2$ and $R^3$.

14. A compound of claim 13 which is 4'-tert-butyl-4-[4-[α-(p-tolyl)benzylidene]piperidino]butyrophenone or a pharmaceutically acceptable acid addition salt thereof.

* * * * *